(12) United States Patent
Sipilä et al.

(10) Patent No.: US 7,233,643 B2
(45) Date of Patent: Jun. 19, 2007

(54) MEASUREMENT APPARATUS AND METHOD FOR DETERMINING THE MATERIAL COMPOSITION OF A SAMPLE BY COMBINED X-RAY FLUORESCENCE ANALYSIS AND LASER-INDUCED BREAKDOWN SPECTROSCOPY

(75) Inventors: Heikki Johannes Sipilä, Espoo (FI); Tero Eklin, Espoo (FI); Kai Kuparinen, Sluntio (FI)

(73) Assignee: Oxford Instruments Analytical Oy (FI)

( * ) Notice: Subject to any disclaimer, the term of this patent is extended or adjusted under 35 U.S.C. 154(b) by 0 days.

(21) Appl. No.: 11/134,740

(22) Filed: May 20, 2005

(65) Prior Publication Data

US 2006/0262900 A1  Nov. 23, 2006

(51) Int. Cl.
*G01N 23/233* (2006.01)
(52) U.S. Cl. .......................... 378/44; 378/45
(58) Field of Classification Search ............ 378/42–49, 378/62, 63, 79, 80, 98, 98.8, 205–208; 372/11, 372/17; 356/317, 318, 417
See application file for complete search history.

(56) References Cited

U.S. PATENT DOCUMENTS

| 5,059,764 | A | * | 10/1991 | Baer | 219/121.68 |
| 5,268,554 | A | * | 12/1993 | Ream | 219/121.8 |
| 5,365,563 | A | * | 11/1994 | Kira et al. | 378/48 |
| 5,583,634 | A | | 12/1996 | Andre et al. | |
| 6,233,307 | B1 | * | 5/2001 | Golenhofen | 378/45 |
| 6,314,158 | B1 | * | 11/2001 | Shiota et al. | 378/48 |
| 6,752,315 | B1 | * | 6/2004 | Damron et al. | 235/454 |
| 6,801,595 | B2 | * | 10/2004 | Grodzins et al. | 378/45 |
| 6,819,694 | B2 | * | 11/2004 | Jiang et al. | 372/45.013 |
| 2002/0168045 | A1 | | 11/2002 | Grodzins et al. | |

OTHER PUBLICATIONS

European Search Report in European Patent Application No. 06113917.6, which corresponds to subject application.
R. Dabu et al. "Design and characterization of an end-pumped Nd:YAG microlaser," *Romanian Report in Physics*, vol. 56, No. 2 pp. 294-305 (2004)—National Institute for Lasers, Plasma, and Radiation Physics, Bucharest, Romania.

* cited by examiner

*Primary Examiner*—Edward J. Glick
*Assistant Examiner*—Irakli Kiknadze
(74) *Attorney, Agent, or Firm*—Wood, Phillips, Katz, Clark & Mortimer

(57) ABSTRACT

A measurement apparatus and method are provided for determining the material composition of a sample. An X-ray fluorescence detector (412) detects fluorescent X-rays coming from said sample under irradiation with incident X-rays. A laser source (301) is adapted to produce a laser beam. Focusing optics (302) focus said laser beam into a focal spot on a surface of said sample. An optical sensor (312) detects optical emissions coming from particles of said sample upon being exposed to said laser beam at said focal spot. A gas administration subsystem (104, 105, 106, 107, 108) is adapted to controllably deliver gas to a space (101) around said focal spot.

21 Claims, 3 Drawing Sheets

MEASUREMENT APPARATUS AND METHOD FOR DETERMINING THE MATERIAL COMPOSITION OF A SAMPLE BY COMBINED X-RAY FLUORESCENCE ANALYSIS AND LASER-INDUCED BREAKDOWN SPECTROSCOPY

TECHNICAL FIELD

The invention concerns the field of portable analyzers adapted to determine the material composition of samples. Especially the invention relates to multimode analysers capable of utilizing both X-ray fluorescence and optical emission spectroscopy; improvements are presented that greatly enhance the applicability of multimode analysers to practical measurement purposes.

BACKGROUND OF THE INVENTION

Determining the material composition of a sample becomes actual in various cases, including but not being limited to acceptance tests of various substances or workpieces, evaluating jewelry and other noble metal products, investigating evidence collected from crime scenes, sorting on scrap yards and controlling industrial processes. Known methods of determining material composition can be roughly classified to chemical and physical processes, of which the latter typically mean exposing a part of the sample to excitation radiation and measuring the obtained response.

X-ray fluorescence (XRF) analysers are known that expose a sample to X-rays coming from a radiation source and collect the fluorescence radiation induced in the atoms and molecules of the sample. By analysing the relative intensity of fluorescent X-rays of different energies it is possible to deduce the relative proportions of various constituents in the sample.

Another known physical process for determining material composition is optical emission spectroscopy (OES), in which a portion of the sample material is heated to the state of plasma, so that the relaxation of excited states in the sample atoms and particles cause the emission of photons at energies that are specific to each atom and particle species. In a manner that is somewhat analogous to X-ray fluorescence analysis, a measured optical emission spectrum can reveal the relative amounts of certain constituents in the sample. In order to create the plasma various techniques can be used: for example an electric arc is ignited between a spark electrode and the surface of the sample, or a laser of high enough intensity is focused onto the surface of the sample. OES based on the last-mentioned technique is also known as LIBS (laser induced breakdown spectroscopy).

A U.S. Pat. No. 6,801,595 is known to disclose an analyser that combines both XRF and OES to a single apparatus. The analyser disclosed in said patent comprises an X-ray source and a fluorescent X-ray detector as well as means for performing optical analysis, preferably LIBS. A processor is arranged to collect the results of both the XRF and the OES measurements, so that both are available for determining the material composition of the sample. However, this apparatus has several drawbacks. The accuracy and reliability of the optical analysis made therewith is often poor, because it is difficult to obtain optical signals that would be high enough in intensity and representative enough of the overall composition of the sample.

SUMMARY OF THE INVENTION

The present invention aims at presenting a combined X-ray and optical analyser for analysing the composition of a sample, with high reliability of measurement results and ease of use.

According to a first aspect of the invention a portable analyser apparatus comprises or is adapted to receive a gas container, from which gaseous medium can be controllably blown to at least one of the focus area and the optical path through which the optical signal reaches the detector. A locally generated protective gas atmosphere at the focus area helps to achieve suitable conditions for creating and maintaining the plasma and furthers the collection of the correct optical signal. Flushing the optical path with a protective gas enhances transmissivity, enabling a larger fraction of the original signal to reach the detector. The optical measurement is relatively fast, which means that the protective gas only needs to be administrated very selectively, so that even a relatively small gas container is sufficient.

According to a second aspect of the invention the measurement apparatus comprises an aiming aid designed to give the user visual feedback about the exact location at which the analysis will be focused. The laser beam used for creating the plasma plume has typically its wavelength in somewhere else than the wavelength range of visible light, which means that it cannot be used to provide any visual feedback. The aiming aid may take conceptually the form of an endoscope, which means that an image of the inspected area is optically transferred to a display or an ocular. If needed, laser light of some other wavelength, specifically of a visible wavelength, can be used as a pointer that produces a visible spot of light at the same location where the plasma-inducing laser will hit.

According to a third aspect of the invention the focal point of the plasma-inducing laser will not be held stationary on the surface of the sample during the measurement, but a relative movement is caused between the focal point and the sample. Basically there are three alternatives: moving the sample in relation to the measurement apparatus, moving the measurement apparatus in relation to the sample, or moving the focal point of the plasma-inducing laser. Of these the last-mentioned is the most feasible. It can be accomplished by using for example a movable mirror or lens, the movement of which causes the optical path to change so that the focal point moves on the surface of the sample. This way a more representative portion of the sample material will be collected to the plasma plume, and the "drilling effect" can be avoided. The last-mentioned means that the laser will not drill a hole to the sample surface.

The exemplary embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE INVENTION

Figure 1:
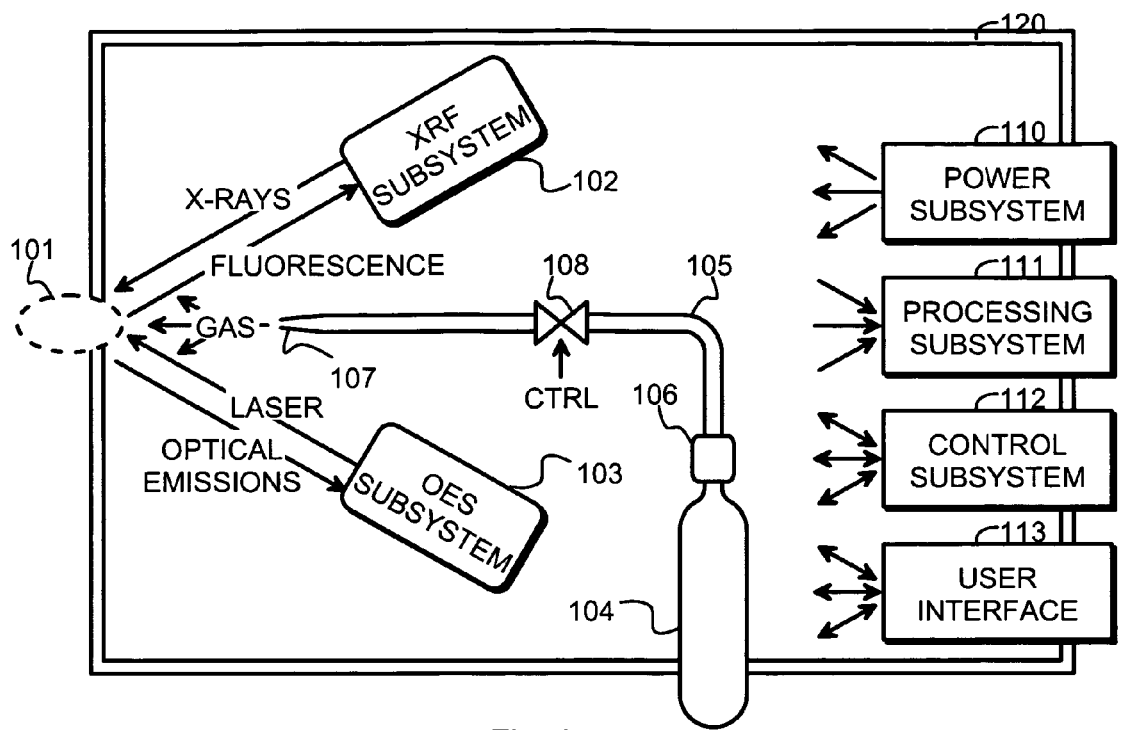
FIG. 1 illustrates a measurement apparatus according to an embodiment of the invention.

FIG. 1 is a schematic block diagram of a measurement apparatus according to an embodiment of the invention. The measurement apparatus is meant for analyzing the material composition of a sample located within a sample area 101. An X-ray fluorescence subsystem 102 (also designated as the XRF subsystem for short) is provided for illuminating a sample with X-rays and for collecting and detecting fluorescent radiation induced in the sample by said X-rays. An optical emission spectroscopy subsystem 103 (also designated as the OES subsystem for short; could likewise be designated as the LIBS subsystem) is provided for focusing a powerful laser beam onto a surface of the sample and for collecting and detecting optical emissions coming from a plasma plume created by said laser beam.

In order to controllably create a local gas atmosphere around the location where the measurement is taking place, the apparatus comprises also a gas administration subsystem, which in FIG. 1 is shown to comprise a gas cylinder 104, a gas conduit 105 and attachment means 106 for attaching the gas cylinder 104 to one end of the gas conduit 105. At the other end of the gas conduit 105 there is a nozzle 107, and a controllable valve 108 is provided for controlling the flow of gas from the gas cylinder 104 through the gas conduit 105 and the nozzle 107 towards the sample area 101. Additionally or alternatively the nozzle 107 may be adapted to direct the gas from the gas conduit 105 to the optical path between the sample area 101 and the OES subsystem 103, and/or to the optical path between the sample area 101 and the XRF subsystem 102.

Other parts of the measurement apparatus include a power subsystem 110 adapted to provide all other parts with the required operating power, a processing subsystem 111 adapted to receive information about detected fluorescence and detected optical emissions from the XRF and OES subsystems 102 and 103 respectively, a control subsystem 112 adapted to control the operation of all controllable parts of the apparatus, as well as a user interface 113 adapted to provide the user with information about the measurement results and overall operation of the apparatus and for offering the user some means for giving inputs. The provision of further functionalities is not excluded; for example a measurement apparatus of this kind typically includes a data exchange connection for coupling it to external computer devices. An outer cover 120 encloses at least a major portion of the other parts shown in FIG. 1.

Figure 2:
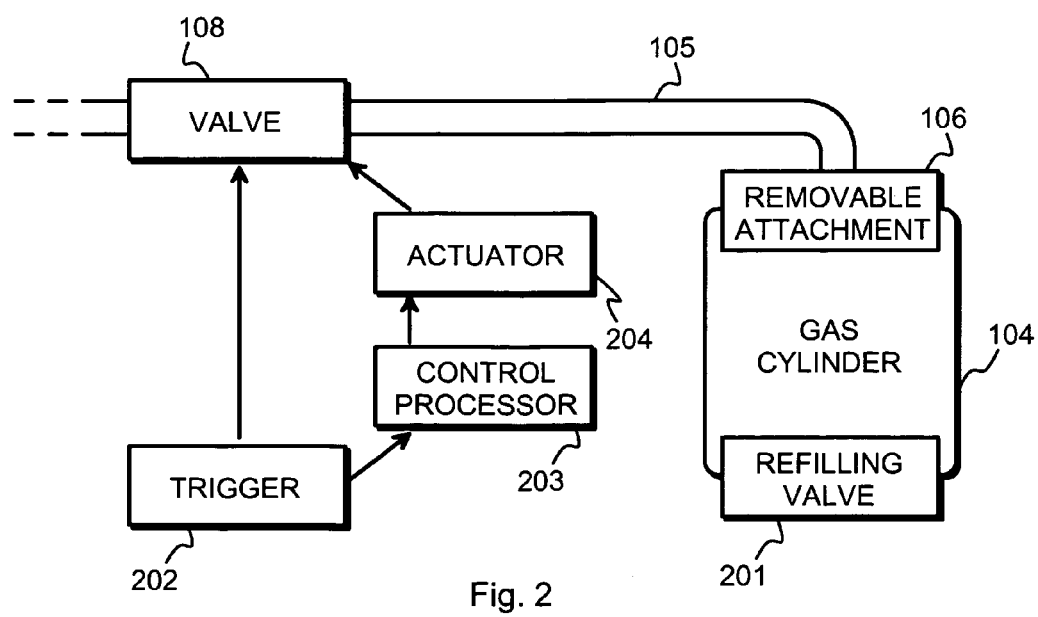
FIG. 2 illustrates details of gas administration according to an embodiment of the invention.

FIG. 2 illustrates some more detailed features of a gas administration subsystem for a measurement apparatus according to an embodiment of the invention. Some of the features illustrated in FIG. 2 are alternatives of each other. In order to make it easy to incorporate the administration of protective gas to a handheld measurement apparatus, it is advantageous to use a relatively small, replaceable gas cartridge as the gas cylinder 104. Replaceable gas cartridges of suitable kind are widely known e.g. from the technology of hand tools powered by pressurized gas, as well as from self-inflating buoyancy products. Using replaceable gas cartridges requires that the attachment means 106 are designed to facilitate easy removal of used gas cartridges and the attachment of fresh ones. Suitable attachment means are likewise known from the technical fields mentioned above as examples. An alternative is to provide the gas cylinder 104 with a refilling valve 201, so that it can be refilled with gas (also) without removing it from the measurement apparatus.

As a part of the user interface of the measurement apparatus, there is most advantageously provided a trigger 202. Pressing or otherwise actuating the trigger 202 causes the controllable valve 108 to open, allowing gas to flow from the gas cylinder 104 through the gas conduit 105 to the sample area. Again, at least two alternative solutions exist. There may be a direct mechanical coupling from the trigger 202 to the controllable valve 108, or actuating the trigger 202 may give an input signal to a control processor 203, which is adapted to interpret this input signal as a command for opening the controllable valve 108. In the last-mentioned case the control processor 203, which in the block diagram of FIG. 1 is a part of the control subsystem 112, is adapted to command an actuator 204 to open the controllable valve 108.

In order not to use more gas than what is needed for a measurement, it is advantageous to somehow ensure that the controllable valve 108 only stays open for as long as the protective gas atmosphere is needed. This time may be as short as in the order of few seconds, because laser-induced OES measurements take place relatively quickly. Mechanical means for regulating the amount of gas delivered in a single shot are known at least from the technology of inhalators used to administrate medical substances in gaseous form to patients. If a combination of a control processor 203 and an actuator 204 is used, it is very simple to program the control processor 203 so that it only tells the actuator 204 to keep the controllable valve 108 open for a predetermined duration of time or otherwise limits the amount of delivered gas.

The use of a noble gas to create a local protective gas atmosphere will improve the analytical performance of light elements, such as e.g. sulphur and phosphorus, in the OES measurement. If the gas is suitably selected, so that it is e.g. helium, it will also improve the performance of the XRF measurement.

Figure 3:
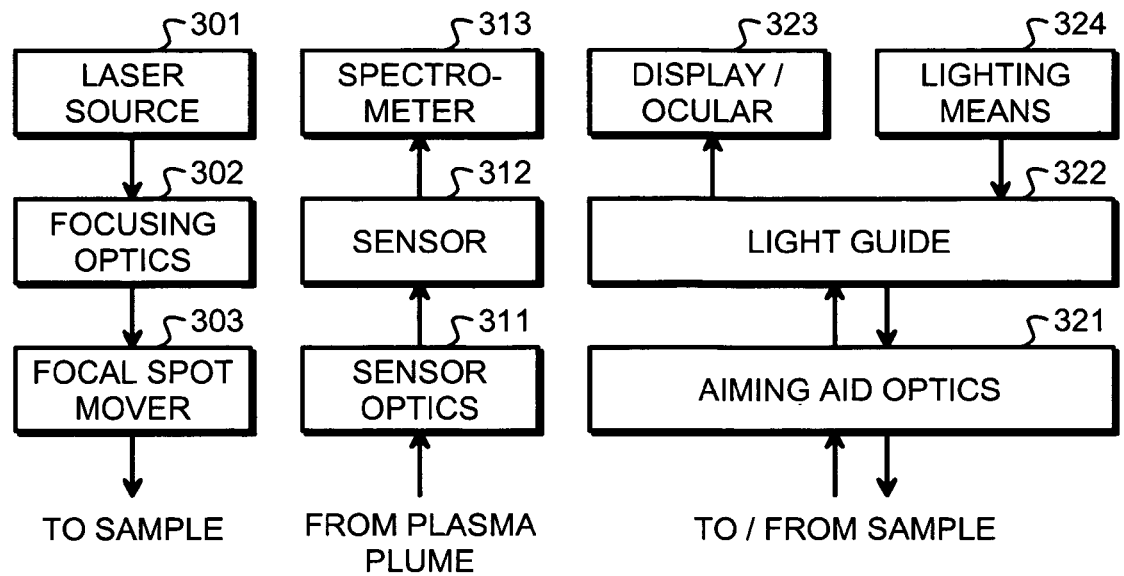
FIG. 3 illustrates an exemplary OES subsystem in an apparatus according to an embodiment of the invention.

FIG. 3 illustrates certain optical side aspects of a measurement apparatus according to an embodiment of the invention. In order to perform laser-induced OES measurements there must be a laser source 301, which is capable of producing a momentary energy density at a focal spot which is high enough to change a small portion of the sample material into a state of plasma. In modern laser-induced OES and LIBS devices it is customary to use a so-called Nd:YAG microlaser, in which a high-brightness laser diode with a small diode aperture creates a so-called pump beam. The carrier wave power of the pump beam is typically in the order of a few watts. A collimating and focusing system concentrates the pump beam on an active medium, typically Nd:YAG (Neodymium (3+)-doped Yttrium Aluminum Garnet), which has a saturable absorber and a coupling mirror attached to one end. The saturable absorber may be for example a slab of $Cr^{4+}$:YAG (Chromium (4+)-doped Yttrium Aluminum Garnet). The output of the Nd:YAG microlaser consists of high-power pulses with pulse duration in the order of nanoseconds. Pulse repetition rate can be controllably varied from monopulse applications to the order of a few kHz. General characteristics of Nd:YAG microlasers are presented for example in the publication R. Dabu, A. Stratan, L. Neagu: "Design and characterization of an end-pumped Nd:YAG microlaser", Romanian Reports in Phisics, Vol. 56, No. 2, pp. 294–305, 2004, which is incorporated herein by reference. Due to the pulse generation mechanism the structure is also known as a passively Q-switched pulse laser.

The stability of the passively Q-switched pulse laser is highly dependent on the output stability of the pump laser. This is especially important in portable applications, where the ambient temperature can easily rise above +40 degrees centigrade. The stability of the output characteristics of laser diodes can be improved by equipping them with appropriately driven Peltier-elements adapted to produce a cooling effect, but this causes a large increase in the overall energy consumption of the apparatus because Peltier elements traditionally have only moderate efficiency. According to a specific embodiment of the present invention the stability problem can be solved by locking the output wavelength of the laser diode. In practice this is most easily accomplished by using a so-called Fabry-Perot filter at the exit of the laser diode, which acts as a bandpass filter that only passes the desired wavelength(s). Fabry-Perot filters, specifically ones implemented with so-called fiber bragg gratings, suitable for this purpose are known e.g. from patent publications U.S. Pat. No. 5,048,913, U.S. Pat. No. 5,104,209 and U.S. Pat. No. 5,216,739.

Instead of a single laser source it is possible to use two or more laser sources producing laser light on different wavelengths, or a single laser source and one or more nonlinear optical crystals such as Potassium Titanyl Phosphate (KTP) crystals and appropriate timing, to vary the way in which the optical stimulus is provided to the sample. With frequency multipliers it is possible to change the initial infrared range wavelength of the plasma-inducing laser light to e.g. one half or one quarter of the original wavelength.

Focusing optics 302 may include, in a way very well known as such, optical elements such as lenses, mirrors, slits, grids, collimators and the like. The task of the focusing optics 302 is to focus the output beam of the laser source 301 onto the surface of a sample. Relatively gentle changes in beam diameter, synonymous with relatively long focal length, are preferred because measurement apparatuses of the kind meant in the invention are frequently used in field conditions, where it is not possible to require very exact positioning of the sample in relation to the measurement head. A long focal length helps to reduce the effect of variations in measurement geometry. However, even if in this context the focal length can be said to be long if it allows an uncertainty of submillimeter scale in sample positioning, it should be understood that in a macroscopic scale (at distances larger than a few millimeters) and from the point of view of a user operating the measurement apparatus, the plasma-inducing laser diverges so quickly and has such a harmless wavelength that radiation hazards to the environment are negligible. Due to the expected difficulties in positioning the sample very exactly we may define that the focal spot is "on the surface of the sample" if it is close enough to the surface (in-or outside the sample material) to allow the formation of plasma.

According to an aspect of the invention there is provided a focal spot mover 303, the task of which is to move the focal spot of the plasma-inducing laser beam across the surface of a sample for a distance that is large compared with the diameter of the focal spot. The purpose of moving the focal spot is to cover a more representative portion of the sample material than what happens to be within the area of the focal spot. Additionally moving the focal spot prevents repeated laser pulses from eating away the surface of the sample material at one point. Although the size of the "drilling hole" created by a stationary focal spot would be so small that it would seldom be even visible, let alone cause any actual disadvantage, the drilling effect may involve other drawbacks for example in applications where the measurement is aimed at investigating the very surface of a sample the material composition of which varies as a function of depth.

Due to the very short duration of each single laser pulse, the movement of the focal spot during a single pulse is negligible and can be omitted. However, when pulses are repeated for a measurement duration in the order of a few seconds, even a relatively simple focal spot mover arrangement is capable of making the focal spot traverse a significant distance, in the order of one millimeter or a few millimeters. The physical implementation of the focal spot mover 303 may involve e.g. an electrically moved mirror or a rotating lense. The movement of the focal spot on the sample surface may be oscillatory, so that it travels e.g. a linerar track back and forth or along a circular or elliptical track. The electric power needed to operate the focal spot mover comes from the power subsystem of the measurement apparatus (see block 110 in FIG. 1) and the moving is accomplished under the control of the control subsystem (see block 112 in FIG. 1). It may be advisable to allow the user to have some online control over the way in which the focal spot is moved, especially if the sample to be investigated is so small or heterogeneous that moving the focal spot might involve the risk of making it wander out of the actual area of interest. Such control is most advantageously combined with the aiming aid discussed in more detail below.

Sensor optics 311 are provided for collecting optical emissions from a plasma plume induced at the focal spot and for directing the collected optical emissions to the optical sensor 312. In their simplest form the sensor optics 311 consist of a free passage of light between the sample surface and the sensor 312. More elaborate solutions may include for example lenses, mirrors, light guides and other optical elements. In order to keep reflected quanta of the incident laser radiation from interfering with the detection of optical emissions it is advantageous to use an infrared filter as a part of the sensor optics 311. A normal Nd:YAG microlaser produces incident radiation at the wavelength of about 1060 nm, which is in the infrared range, so it is effectively filtered out by an infrared filter.

The sensor 312 detects the optical emissions collected by the sensor optics 311. In order to provide meaningful results the sensor 312 must be sensitive to wavelength and intensity. However, these requirements are relatively easily filled. A line of photodiodes, similar to those used in regular barcode scanners, is often sufficient. The sensor 312 is coupled to a spectrometer 313, which is an electronic circuit adapted to read the detection results from the sensor 312 so that information about spectral distribution and intensity is preserved, and to integrate consecutive readings over a predetermined time. Together, the sensor 312 and the spectrometer 313 constitute an arrangement adapted to convert the collected optical emissions into an electronic signal representative of the spectral distribution and intensity of the optical emissions. If a focal point mover is used to move the focal spot of the plasma-inducing laser, the detection process must be adapted to take into account the corresponding changes in measurement geometry. This can be easily accomplished for example by using the movable mirror that causes the focal spot to move also as a part of the sensor optics 311.

According to an aspect of the invention, the measurement apparatus comprises an optical aiming aid adapted to provide the user with visual feedback about the location on the sample surface that will be subjected to measurement. An image of the appropriate part of the sample surface is conducted through aiming aid optics 321 and a light guide 322 to a display or ocular 323, which we will designate as the display device. In order to ensure sufficient lighting of the sample it is advisable to provide lighting means 324, from which light can be taken through the light guide 322 and aiming aid optics 321 to the target area on the sample surface.

According to a first alternative, the lighting means 324 produce a general background lighting in order to provide a sufficiently bright image of the target area on the sample surface to the display device. Other aiming means, such as frames and/or crosshairs, can then be used to indicate, exactly which point on the sample surface the laser beam from the laser source 301 will hit.

According to another alternative, the lighting means 324 may comprise another laser source, which in contrast to the plasma-inducing laser source 301 is adapted to produce a laser beam in the visible wavelength range. This visible laser beam can be focused through the light guide 322 and the aiming aid optics 321 onto the sample surface, where its reflection constitutes a visible indicator spot that shows, which point on the sample surface the laser beam from the laser source 301 will hit. In order to keep the indicator laser from interfering with the optical measurement it is advisable to make its operation controllable so that it will be shut off during the optical measurement. Alternatively filtering arrangements can be utilized.

The light guide 322, the aiming aid optics 321, the focusing optics 302 and the focal spot mover 303 may include shared components. For example, also the visible laser beam originating from the lighting means 324 may be directed through the focal spot mover 303 in order to move the indicator spot on the sample surface in a manner that is similar to the movement of the focal spot of the plasma-inducing laser beam. This way the user can easily check, in the case of a very small or very heterogeneous sample, that the movement of the focal spot will not take it outside the area of interest. If the movement caused by the focal spot mover 303 is controllable, the user may first check it by using the indicator spot and by changing e.g. the extent or direction of linear movement or the radius of a circular movement so that only an appropriate target area of the sample surface will be covered by the movement of the focal spot. Controlling the movement caused by the focal spot mover 303 necessitates movement-controlling input means in the user interface of the measurement apparatus, as well as a coupling from these to a part of the control subsystem that actually controls the focal spot mover 303.

Figure 4:
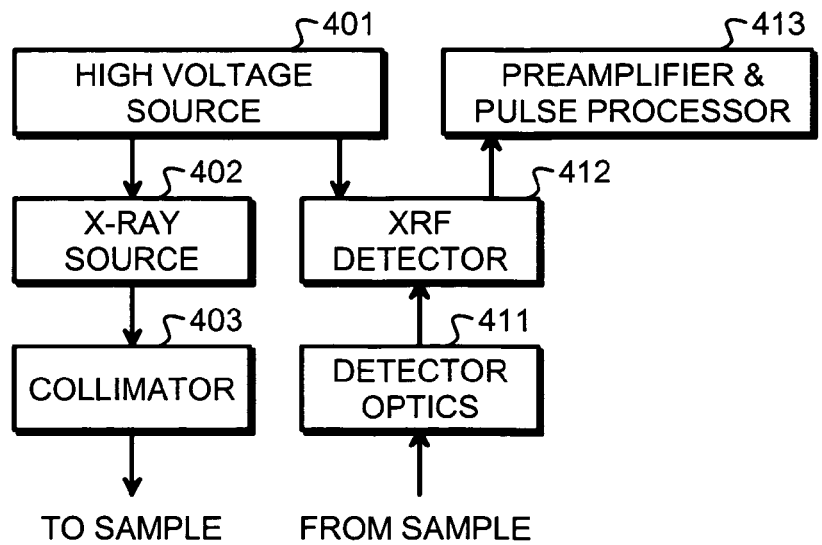
FIG. 4 illustrates an exemplary XRF subsystem in an apparatus according to an embodiment of the invention.

FIG. 4 illustrates schematically parts of an exemplary XRF subsystem. A high voltage source 401 generates the required kV range voltage(s) from the normally available operating voltage(s). The X-ray source 402 is preferably an X-ray tube, because in comparison with radioactive source substances it has the significant advantage of not producing any radiation when the power is off. A collimator 403 collimates the X-rays coming from the X-ray source 402 towards the sample. It is also possible to use an external X-ray source for irradiating the sample, in which case the measurement apparatus according to the invention would not need to have any internal X-ray source or collimator at all. Some kind of detector optics 411 may be used to direct the fluorescent radiation to an X-ray fluorescence detector 412, which is preferably a solid-state semiconductor detector and receives the necessary high bias voltage(s) from the high voltage source 401. The output of the X-ray fluorescence detector 412 is coupled to a preamplifier and pulse processor arrangement 413.

Figure 5:
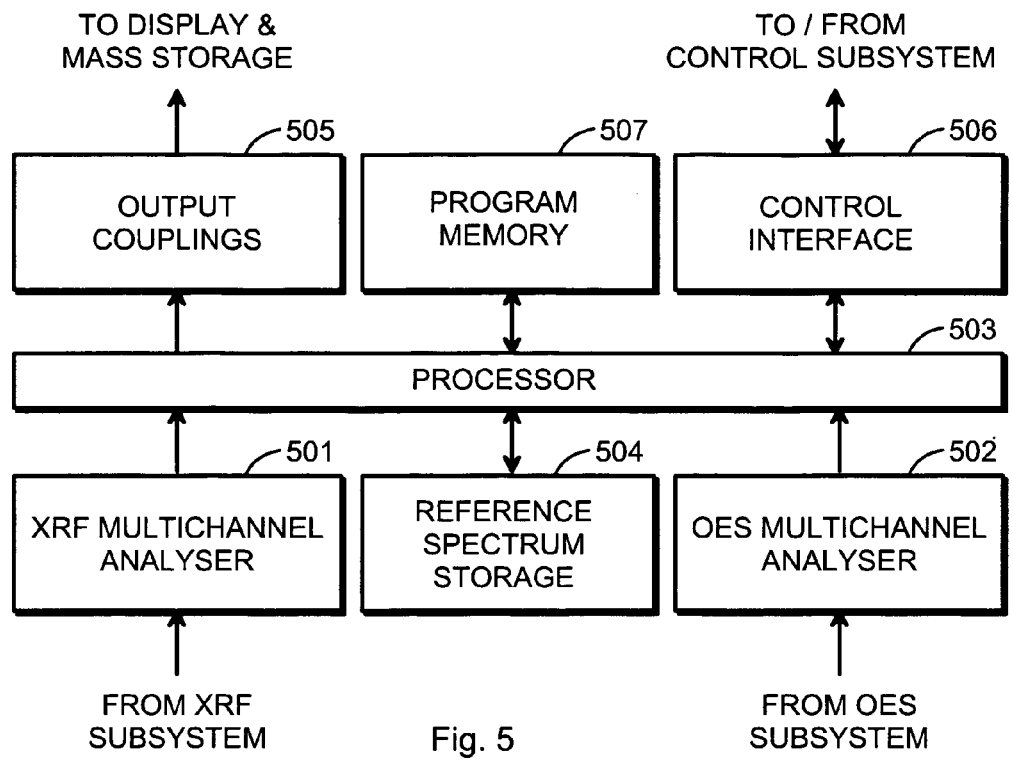
FIG. 5 illustrates an exemplary processing subsystem in an apparatus according to an embodiment of the invention.

FIG. 5 illustrates schematically parts of an exemplary processing subsystem. An XRF multichannel analyzer 501 collects the pulses from the output of the preamplifier and pulse processor of the XRF subsystem, and classifies them into energyspecific bins so that as a whole the collected pulses will constitute an X-ray fluorescence spectrum. Similarly an OES multichannel analyzer 502 collects the output information from the OES subsystem into an optical spectrum. A processor 503 is adapted to compare the measured spectra with reference information stored in a reference spectrum storage 504. Typically the processor 503 is adapted to use the XRF measurement for coarse determination of the material composition of the sample, and use such obtained information to select a limited portion of OES calibration curve sets for refining the previous result. Output information is taken through output couplings 505 to e.g. a display and/or a mass storage. A control interface 506 is provided to link the processing subsystem to the control subsystem. The programs executed by the processor 503 are stored in a program memory 507.

The control subsystem of a measurement apparatus according to the invention is essentially a processor or a corresponding programmable device, adapted to exchange commands, instructions and other information with other parts of the apparatus and to execute programmed instructions for controlling the operation of the apparatus. The division into a control subsystem and a processing subsystem may be somewhat blurred, because they can both be built around the same processor.

Figure 6:
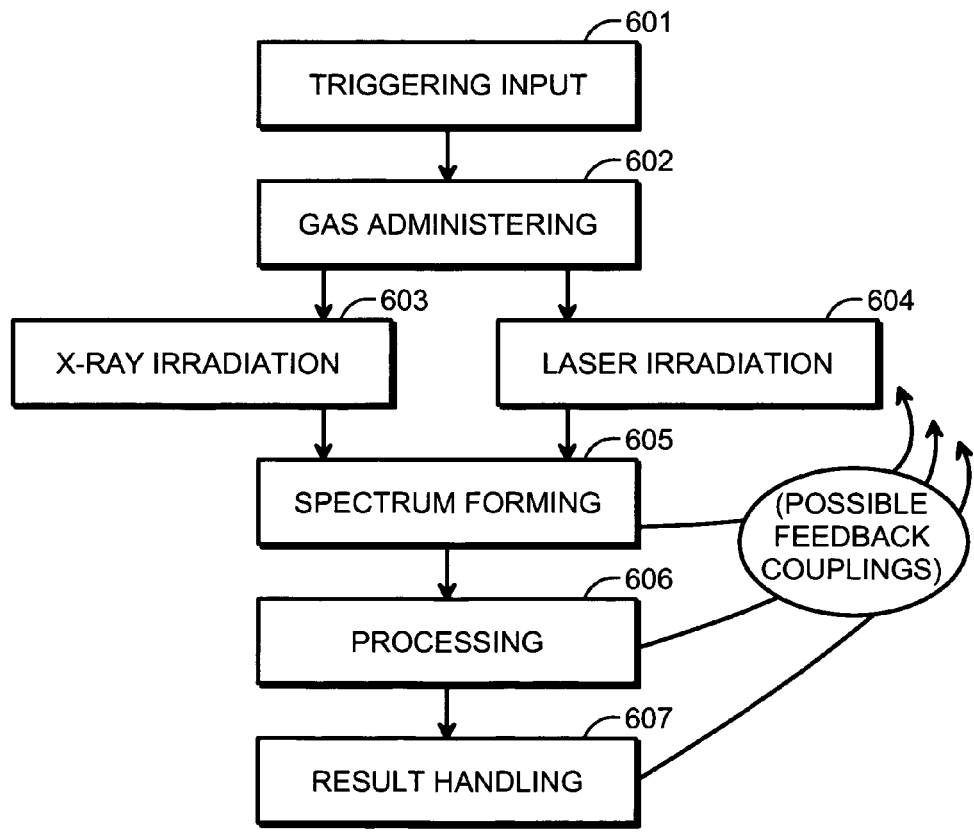
FIG. 6 illustrates aspects of a method according to an embodiment of the invention.

FIG. 6 illustrates some method aspects of the invention. A measurement begins when a triggering input is received at step 601. Typically a user pulls a measurement trigger or otherwise performs an action that gives the measurement apparatus a signal to start measuring. If an aiming aid is used, illuminating an area of the sample surface and displaying an image of at least a part of the illuminated area to a user may be thought to be incorporated in step 601.

Gas is administrated to the target area at step 602, preferably (but not mandatorily) before irradiation with the fluorescence-inducing X-rays and the plasma-inducing laser begin at steps 603 and 604 respectively. The irradiation steps 603 and 604 may take place simultaneously or in succession, in either order. Exposure times in OES are typically much shorter than in XRF: for an analysis that requires 60–120 seconds of X-ray exposure and fluorescence detection an optical exposure time of only few seconds may be sufficient.

Spectra are collected at step 605, results are processed at step 606 and the processed results are directed to display and/or mass storage at the results handling step 607. From one or more of steps 605, 606 and 607 there may be feedback couplings to the previous steps of the method. For example, if the XRF measurement is performed without gas and the necessary puff of gas is only given for the duration of the optical measurement (which typically requires the administation of gas to be electronically controlled), the method may proceed first through steps 601, 603, 605 and 606. After the processing subsystem has found that the XRF measurement has given enough results for reliably estimating the coarse material composition of the sample, it gives in indication which in the schematic representation of FIG. 6 appears as a feedback jump to step 602, from which the method proceeds through steps 604, 605 and 606 to step 607. Another exemplary way of utilizing feedback is to keep at least one of the irradiation steps active until an indication from results processing tells that enough fluorescent quanta and/or enough optical emissions have been received, after which the radiation source(s) is/are shut off.

We claim:

1. A measurement apparatus for determining the material composition of a sample, comprising:
    an X-ray fluorescence detector adapted to detect fluorescent X-rays coming from said sample upon said sample being exposed to incident X-rays,
    a laser source adapted to produce a laser beam,
    focusing optics adapted to focus said laser beam into a focal spot on a surface of said sample,
    an optical sensor adapted to detect optical emissions coming from particles of said sample upon said sample being exposed to said laser beam at said focal spot, and
    a gas administration subsystem adapted to controllably deliver noble gas to a space around said focal spot;
    wherein the measurement apparatus is a portable measurement apparatus, and wherein the measurement apparatus is configured to use a shorter exposure time in an optical measurement involving the use of said laser source, said focusing optics and said optical sensor than in an X-ray fluorescence measurement involving the use of said X-ray fluorescence detector, and wherein said gas administration subsystem is configured to stop delivering the noble gas when said optical measurement ends.

2. A measurement apparatus according to claim 1, comprising:
    a gas conduit
    attachment means for attaching a gas cylinder to one end of said gas conduit,
    a nozzle at another end of said gas conduit, said nozzle being directed towards said space around said focal spot and
    a controllable valve along said gas conduit, said controllable valve being adapted to open and close said gas conduit as a response to user action.

3. A measurement apparatus according to claim 2, comprising a trigger and a mechanical coupling between said trigger and said controllable valve.

4. A measurement apparatus according to claim 2, comprising a trigger, a con-trol processor adapted to receive an input signal from said trigger, and an actuator adapted to receive a command from said control processor as a response to an input signal from said trigger to said control processor and adapted to open said controllable valve as a response to said command.

5. A measurement apparatus according to claim 2, wherein said attachment means are adapted to removably receive a replaceable gas cartridge.

6. A measurement apparatus according to claim 5, comprising an outer cover adapted to at least partly enclose a replaceable gas cartridge attached to said at-tachment means.

7. A measurement apparatus according to claim 2, comprising a gas cylinder at-tached to said attachment means and a refilling valve for refilling said gas cylinder.

8. A measurement apparatus according to claim 1, comprising a focal spot mover adapted to move said focal spot on said surface of said sample during a measurement.

9. A measurement apparatus according to claim 8, wherein said focal spot mover comprises a movable mirror.

10. A measurement apparatus according to claim 1, wherein said laser source is a passively Q-switched pulse laser comprising a laser diode, an active medium and a saturable absorber.

11. A measurement apparatus according to claim 10, comprising a Fabry-Perot filter between said laser diode and said active medium for locking the output wave-length of said laser diode.

12. A measurement apparatus according to claim 10, comprising an infrared filter between said space around said focal spot and said optical sensor, for keeping reflections of said laser beam from interfering with the detection of optical emissions.

13. A measurement apparatus according to claim 1, comprising an optical aiming aid adapted to provide a user with visual feedback about the location of said focal spot on said surface of said sample.

14. A measurement apparatus according to claim 13, wherein said optical aiming aid comprises:
    a display device and
    aiming aid optics and a light guide adapted to conduct an image of a part of the sample surface to said display device.

15. A measurement apparatus according to claim 14, comprising aiming means adapted to indicate on said display device at which point on the sample surface the focal spot will be.

16. A measurement apparatus according to claim 14, comprising a source of laser light of visible wavelength adapted to illuminate a spot on said surface of said sample, said illuminated spot being coincident with said focal spot.

17. A method for determining the material composition of a sample, comprising:
    irradiating said sample with incident X-rays,
    detecting fluorescent X-rays coming from said sample,
    producing a laser beam and focusing said laser beam into a focal spot on a surface of said sample,
    detecting optical emissions coming from particles of said sample upon said sample being exposed to said laser beam at said focal spot, and
    controllably delivering noble gas to a space around said focal spot;
    wherein the method comprises using a portable measurement apparatus, and wherein an exposure time involving said detection of optical emissions is shorter than an X-ray fluorescence measurement involving said detection of fluorescent X-rays, and wherein said delivering of the noble gas is stopped when said optical measurement ends.

18. A method according to claim 17, comprising:
    preliminarily determining the material composition of said sample on the basis of the spectral distribution of said fluorescent X-rays,
    based on said preliminary determining, selecting a limited number of previously stored optical emission reference spectra and refining the determination of the material composition of said sample on the basis of comparing the spectral distribution of said optical emissions to at least one the selected optical emission reference spectra.

19. A method according to claim 17, comprising moving said focal spot across said surface of said sample during the detection of optical emissions.

20. A method according to claim 17, comprising illuminating an area of said surface of said sample and displaying an image of at least a part of the illuminated area to a user.

21. A method according to claim 20, comprising directing a laser beam of visible wavelength to a location on said surface of said sample coincident with the location of said focal spot.

* * * * *